US009775593B2

(12) United States Patent
Bennett, III

(10) Patent No.: US 9,775,593 B2
(45) Date of Patent: *Oct. 3, 2017

(54) LAPAROSCOPIC PORT SITE CLOSURE TOOL

(71) Applicant: TELEFLEX MEDICAL INCORPORATED, Research Triangle Park, NC (US)

(72) Inventor: Richard M. Bennett, III, Carmel, IN (US)

(73) Assignee: TELEFLEX MEDICAL INCORPORATED, Morrisville, NC (US)

( * ) Notice: Subject to any disclaimer, the term of this patent is extended or adjusted under 35 U.S.C. 154(b) by 182 days.

This patent is subject to a terminal disclaimer.

(21) Appl. No.: 14/672,924

(22) Filed: Mar. 30, 2015

(65) Prior Publication Data

US 2015/0201920 A1    Jul. 23, 2015

Related U.S. Application Data

(63) Continuation of application No. 11/176,616, filed on Jul. 7, 2005, now Pat. No. 8,992,549.

(Continued)

(51) Int. Cl.
*A61B 17/04* (2006.01)
*A61B 17/00* (2006.01)
*A61B 17/06* (2006.01)

(52) U.S. Cl.
CPC ...... *A61B 17/0057* (2013.01); *A61B 17/0482* (2013.01); *A61B 17/0483* (2013.01); *A61B 17/06066* (2013.01); *A61B 2017/00637* (2013.01); *A61B 2017/00663* (2013.01); *A61B 2017/06057* (2013.01)

(58) Field of Classification Search
CPC ............ A61B 17/0057; A61B 17/0482; A61B 2017/06057; A61B 2017/00637; A61B 2017/00663

See application file for complete search history.

(56) References Cited

U.S. PATENT DOCUMENTS 2,646,045 A    7/1953   Priestley
3,361,382 A    1/1968   Converse
(Continued)

FOREIGN PATENT DOCUMENTS

SU          1093329 A1    5/1984
WO     WO2007025302 A3   11/2007

*Primary Examiner* — Katherine Rodjom
(74) *Attorney, Agent, or Firm* — Baker and Hostetler LLP

(57) ABSTRACT

A device is provided to assist in closing an incision through body tissue that comprises a tubular body sized for introduction through the incision and carrying a plurality of stabilizer elements at the distal end thereof. The stabilizer elements are configured to be deployed within the body cavity to engage the lowermost tissue layer. In one method, the device is pulled with the stabilizer elements deployed to retract the body tissue away from adjacent body structure. In another method, a plurality of needle tips carrying sutures are guided through the body tissue to a retention device at the ends of the stabilizer elements. With the needle tips captured in the retention devices, the device is withdrawn from the incision so that the sutures form ligatures that can be tied off to close the incision.

20 Claims, 13 Drawing Sheets

Related U.S. Application Data

(60) Provisional application No. 60/598,798, filed on Aug. 5, 2004.

(56) References Cited

U.S. PATENT DOCUMENTS

| | | |
|---|---|---|
| 3,399,668 A | 9/1968 | Lundgren |
| 3,577,991 A | 5/1971 | Wilkinson |
| 4,345,602 A | 8/1982 | Yoshimura et al. |
| 4,493,323 A | 1/1985 | Albright et al. |
| 4,526,173 A | 7/1985 | Sheehan |
| 4,553,543 A | 11/1985 | Amarasinghe |
| 4,621,640 A | 11/1986 | Mulhollan et al. |
| 4,674,501 A | 6/1987 | Greenberg |
| 4,744,353 A | 5/1988 | McFarland |
| 4,744,364 A | 5/1988 | Kensey |
| 4,899,743 A | 2/1990 | Nicholson et al. |
| 4,938,214 A | 7/1990 | Specht et al. |
| 4,950,273 A | 8/1990 | Briggs |
| 4,955,384 A | 9/1990 | Taylor et al. |
| 4,995,865 A | 2/1991 | Gahara et al. |
| 5,009,663 A | 4/1991 | Broome |
| 5,015,250 A | 5/1991 | Foster |
| 5,037,433 A | 8/1991 | Wilk et al. |
| 5,041,129 A | 8/1991 | Hayhurst et al. |
| 5,053,043 A | 10/1991 | Gottesman et al. |
| 5,078,721 A | 1/1992 | McKeating |
| 5,100,417 A | 3/1992 | Cerier et al. |
| 5,127,785 A | 7/1992 | Faucher |
| 5,147,373 A | 9/1992 | Ferzli |
| 5,171,256 A | 12/1992 | Smith et al. |
| 5,171,257 A | 12/1992 | Ferzli |
| 5,176,691 A | 1/1993 | Pierce |
| 5,181,919 A | 1/1993 | Bergman et al. |
| 5,192,298 A | 3/1993 | Smith et al. |
| 5,196,023 A | 3/1993 | Martin |
| 5,201,743 A | 4/1993 | Haber et al. |
| 5,201,744 A | 4/1993 | Jones |
| 5,201,752 A | 4/1993 | Brown et al. |
| 5,201,759 A | 4/1993 | Ferzli |
| 5,211,655 A | 5/1993 | Hasson |
| 5,220,926 A | 6/1993 | Jones |
| 5,222,508 A | 6/1993 | Contarini |
| 5,222,977 A | 6/1993 | Esser |
| 5,226,899 A | 7/1993 | Lee et al. |
| 5,234,444 A | 8/1993 | Christoudias |
| 5,269,772 A | 12/1993 | Wilk |
| 5,281,237 A | 1/1994 | Gimpelson |
| 5,304,184 A | 4/1994 | Hathaway et al. |
| 5,306,278 A | 4/1994 | Dahl et al. |
| 5,308,358 A | 5/1994 | Bond et al. |
| 5,320,632 A | 6/1994 | Heidmueller |
| 5,334,200 A | 8/1994 | Johnson |
| 5,342,391 A | 8/1994 | Foshee et al. |
| 5,364,408 A | 11/1994 | Gordon |
| 5,374,275 A | 12/1994 | Bradley et al. |
| 5,387,221 A | 2/1995 | Bisgaard |
| 5,391,182 A | 2/1995 | Chin |
| 5,417,699 A | 5/1995 | Klein et al. |
| 5,458,609 A | 10/1995 | Gordon et al. |
| 5,476,469 A | 12/1995 | Hathaway et al. |
| 5,480,409 A | 1/1996 | Riza |
| 5,496,332 A | 3/1996 | Sierra et al. |
| 5,496,335 A | 3/1996 | Thomason et al. |
| 5,501,692 A | 3/1996 | Riza |
| 5,507,755 A | 4/1996 | Gresl et al. |
| 5,507,758 A | 4/1996 | Thomason et al. |
| 5,522,839 A | 6/1996 | Pilling |
| 5,527,321 A | 6/1996 | Hinchliffe |
| 5,527,322 A | 6/1996 | Klein et al. |
| 5,562,686 A | 10/1996 | Sauer et al. |
| 5,562,688 A | 10/1996 | Riza |
| 5,571,117 A | 11/1996 | Ahn |
| 5,573,495 A | 11/1996 | Adler |
| 5,601,576 A | 2/1997 | Garrison |
| 5,613,974 A | 3/1997 | Andreas et al. |
| 5,700,273 A | 12/1997 | Buelna et al. |
| 5,716,369 A | 2/1998 | Riza |
| 5,746,755 A | 5/1998 | Wood et al. |
| 5,772,678 A | 6/1998 | Thomason et al. |
| 5,782,749 A | 7/1998 | Riza |
| 5,792,152 A | 8/1998 | Klein et al. |
| 5,810,850 A | 9/1998 | Hathaway et al. |
| 5,817,111 A | 10/1998 | Riza |
| 5,827,299 A | 10/1998 | Thomason et al. |
| 5,827,300 A | 10/1998 | Fleega |
| 5,843,122 A | 12/1998 | Riza |
| 5,860,990 A | 1/1999 | Nobles et al. |
| 5,868,784 A | 2/1999 | Riza |
| 5,899,911 A | 5/1999 | Carter |
| 5,921,918 A | 7/1999 | Riza |
| 5,928,256 A | 7/1999 | Riza |
| 5,935,126 A | 8/1999 | Riza |
| 5,954,732 A | 9/1999 | Hart et al. |
| 5,954,734 A | 9/1999 | Thomason et al. |
| 5,993,471 A | 11/1999 | Riza et al. |
| 6,059,800 A | 5/2000 | Hart et al. |
| 6,117,144 A | 9/2000 | Nobles et al. |
| 6,136,010 A | 10/2000 | Modesitt et al. |
| 6,183,485 B1 | 2/2001 | Thomason et al. |
| 6,245,079 B1 | 6/2001 | Nobles et al. |
| 6,383,199 B2 | 5/2002 | Carter et al. |
| 6,464,691 B1 | 10/2002 | Castaneda et al. |
| 6,517,553 B2 | 2/2003 | Klein et al. |
| 6,551,331 B2 | 4/2003 | Nobles et al. |
| 6,562,052 B2 | 5/2003 | Nobles et al. |
| 6,911,034 B2 | 6/2005 | Nobles et al. |
| 6,939,356 B2 | 9/2005 | Debbas |
| 7,911,905 B2 | 3/2011 | Park |
| 8,992,549 B2* | 3/2015 | Bennett, III ........ A61B 17/0057 606/144 |
| 2002/0045908 A1* | 4/2002 | Nobles ............... A61B 17/0057 606/144 |
| 2004/0068273 A1* | 4/2004 | Fariss ................ A61B 17/0057 606/144 |
| 2004/0199185 A1 | 10/2004 | Davignon |
| 2006/0030868 A1 | 2/2006 | Bennett |
| 2007/0203507 A1 | 8/2007 | McLaughlin et al. |
| 2008/0033459 A1 | 2/2008 | Shafi et al. |

* cited by examiner

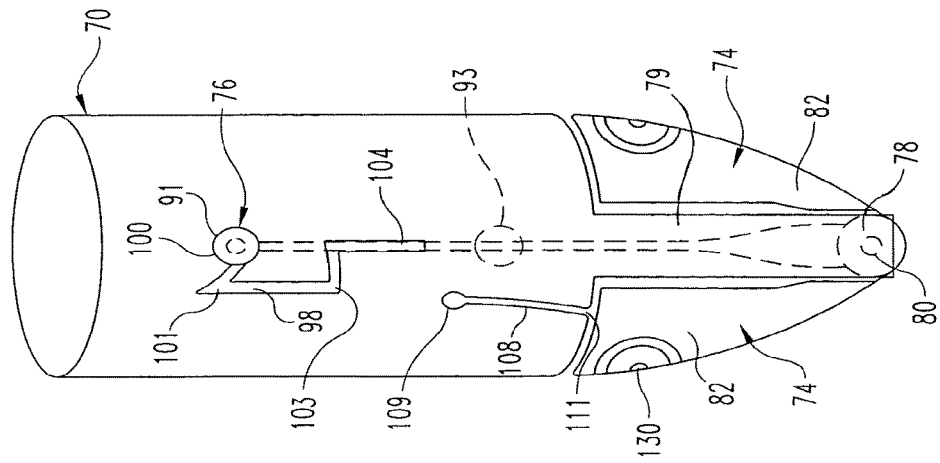
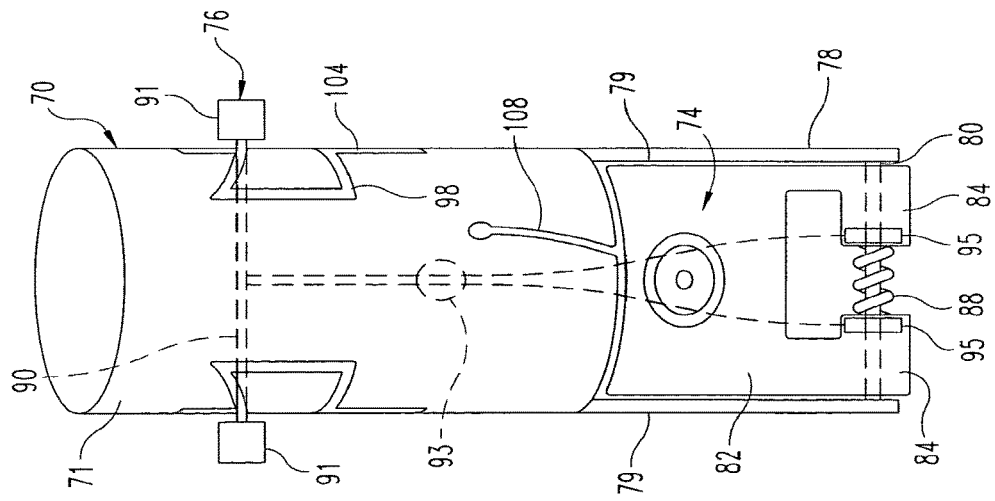

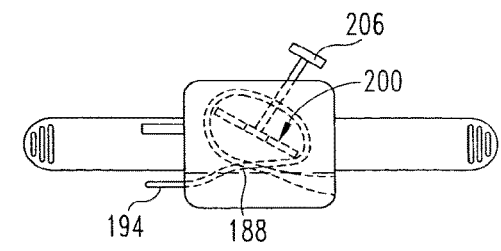
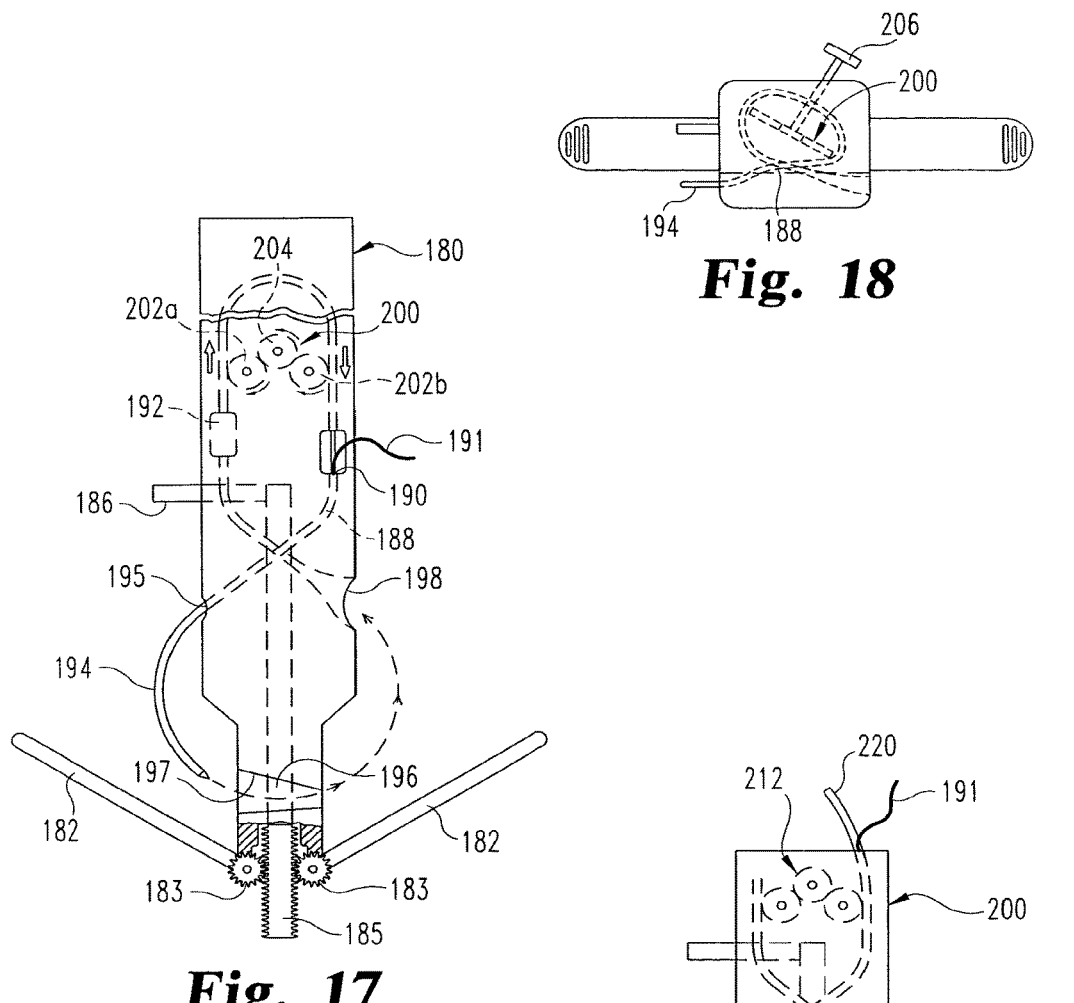
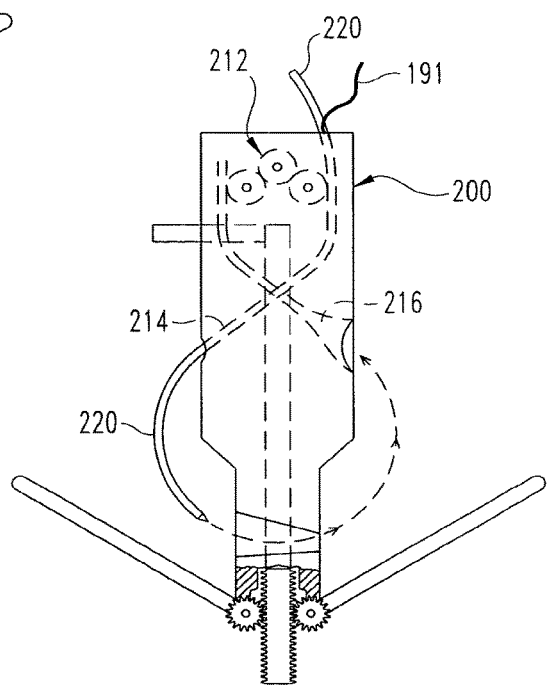

LAPAROSCOPIC PORT SITE CLOSURE TOOL

CROSS-REFERENCE TO RELATED APPLICATIONS

This application is a continuation of U.S. patent application Ser. No. 11/176,616, filed on Jul. 7, 2005, which claims priority to U.S. Provisional Application No. 60/598,798, filed on Aug. 5, 2004, the disclosures and figures of which are incorporated herein by reference.

BACKGROUND OF THE INVENTION

The invention relates generally to surgical suturing devices, and more particularly to intra-abdominal suturing devices designed for closing puncture wounds created by surgical trocars and similar puncturing devices.

Minimally invasive surgery is a revolutionary new technique that has replaced many standard invasive surgical operations requiring large incisions with operations utilizing very small incisions. In this technique, access to the surgical field is made through very small incisions (generally 5-18 mm in diameter) via a surgical trocar. These trocars typically have a diameter of, for example, between 3 mm and 30 mm and a length of about 150 mm (6 inches). Tubes are then inserted through the incision to permit the further introduction of miniaturized instruments and laparoscopes that can be manipulated by a surgeon while viewing the surgical field on a television monitor. This technology affords the patient considerably less pain and disfigurement, and a much faster recovery. The rapid return of the patient to productive activity further reduces the ultimate cost of the surgery.

Although trocars are widely used to puncture the abdominal wall as a first step in minimally invasive surgical techniques, such use creates several clinical problems. The very small size of the incision and the somewhat awkward access to the interior facies of the tissues surrounding the incision make closure of the incision problematic and time consuming. For example, one method requires the introduction of a pre-threaded suture needle approximately 3-5 mm from the edge of the original trocar incision. The surgeon views the needle via a laparoscope as it pierces the abdominal wall. The surgeon then grasps the ligature in the pre-threaded needle with a forceps, eventually secures it, passes it to a needle that has been introduced on the opposite side of the surgical defect, and withdraws the needle up through the other side of the incision, through the abdominal wall, and ties off the suture. The knot is generally tied under the skin to avoid residual external scarring.

Because the surgeon cannot directly visualize the exact position of the needle until after it has passed completely through the abdominal wall, several insertions may be required in order to place the needle at an ideal and proper distance from the trocar incision. The distance from the needle location to the original incision is critical in that the needle must be far enough from the trocar incision to secure an optimal amount of abdominal wall tissue. If the needle distance from the incision is too small, an insufficient amount of tissue will be secured with a consequent risk of inadequate closure of the surgical defect. This may result in subsequent herniation of the omentum or bowel. However, if needle distance from the point of the original trocar incision is too great, incision closure will result in excessive tissue being grasped, and the patient will be left with an unsightly "knot" of tissue. Aside from attendant awkwardness and the problems resulting therefrom, this method is time-consuming and often produces only marginal closure integrity.

Another difficulty associated with this mode for closure is associated with obese patients who present considerable fat in the abdominal region. Because the abdominal wall of an obese patient may be several inches thick, it is extremely difficult, tedious and time consuming to approximate the fascial tissues with a suture. Often times, following removal of a large trocar, the puncture site needs to be enlarged to accomplish this, thus negating some of the advantages of endoscopic surgery previously discussed.

Another common technique for closing a trocar incision comprises the re-approximation of the fascia and subcutaneous fat by means of a small needle introduced through the trocar skin incision from outside the body at the termination of the procedure. The difficulty with this technique is that the edges of the fascia are not easily visualized, with the result that tying the ligature may or may not effectively re-approximate the edges of the fascia. Certainly the peritoneal defect is not effectively closed by this approach because the suture is not placed deeply enough.

Often times, closure of the trocar incision is nothing more than skin deep, the deeper layers of the fascia remaining free. Failure to make complete closure of the incision entails a significant risk of delayed bleeding (occurring after the abdomen is deflated and the tamponading effect of the inflated abdomen ceases), or the possibility of herniation of either omentum or bowel into the subcutaneous opening.

Occasionally, the peritoneal defect may be approximated by a traditional, curved-needle suture ligature that is placed from within the abdominal cavity under direct vision. The knot is then tied either by means of an intra-corporeal or extra-corporeal knot-tying technique. This approach is rarely used because it is cumbersome, requires a high level of skill, and is still not optimal as it ensures only that the peritoneum is closed, closure of the more exterior fascia being purely speculative.

In view of the foregoing there is a clear need for a closure tool or suturing device, and a method of incision closure, that is accurate and reliable, and that does not require an excessive amount of time to complete. There also exists a need for a surgical device and method that can be utilized by surgeons having various skill levels.

SUMMARY OF THE INVENTION

In view of these needs, the present invention contemplates a closure tool that in the first instance applies pressure to the suture site from inside the abdominal cavity, and in the second instance provides a simple, quick-operating mechanism for passing the suture through the body tissue.

In one aspect of the invention, a device is provided for assisting in the closure of the interior tissue layers of a patient. In one embodiment, the device comprises a tubular body configured for introduction through the incision, the body having a distal end and a proximal end and a length between the distal and proximal ends sized so that the distal end may be positioned adjacent the innermost tissue layer while the proximal end is accessible outside the patient. At least one stabilizer element is movably supported at the distal end of the tubular body, the stabilizer element movable relative to the tubular body between an insertion position substantially in alignment with the tubular body for insertion through the incision and a stabilizing position in contact with the interior surface of the innermost tissue layer. The device further comprises means for holding the stabilizer element in the stabilizing position. In this position, the tubular body may be pulled outward relative to the incision so that the stabilizer element engages and retracts the tissue layers relative to body structures adjacent the incision.

In the preferred embodiment, the stabilizer elements include a pair of wings pivotably mounted to the distal end of the tubular body. The wings are supported on an axle extending between a pair of legs extending from the lower edge of the tubular body. A torsion spring helps bias the legs to their extended or stabilizing position. An actuator is provided that is accessible outside the patient that can be manipulated to move the stabilizer elements from their insertion position to their stabilizing position, and then to a removal position when it is desired to withdraw the device from the incision.

In certain embodiments, the stabilizing elements include a retention device at a free end thereof. The retention device is configured to retain a needle tip. The tubular body defines at least one guide channel configured to receive a needle tip carrying a suture. The guide channel is arranged so that a needle tip passing therethrough will be in alignment with the retention device when the stabilizing element is in its stabilizing position.

Thus, in one method of the invention, a needle guide is used to advance a needle tip carrying a suture through body tissue disposed between the tubular body and the stabilizer elements. Once the needle tip reaches the stabilizer element, the tip is captured by the retention device, so that the suture is in effect tied to the stabilizer element. With the needle tips captured in corresponding stabilizer elements, the elements are moved to a removal position so that the device may be removed from the incision. As the device is removed, the sutures are pulled through the tissue and the incision to form ligatures at multiple locations. The ligatures may then be cut from the device and tied off in a known manner to close the incision.

In one aspect of the invention, the needle tips are removably engaged to a corresponding needle driver. Once the needle driver has pushed the needle tip into the retention element, the driver is removed. In another embodiment, the needle driver is configured to drive the needle tip through an arcuate path in which the needle tip moves from the tubular body, through the body tissue on opposite sides of the incision and back into a retention element formed in the tubular body itself.

In accordance with one embodiment of the invention, a method is provided for assisting in the closure of an incision in body tissue comprising: introducing a tubular body through the incision; deploying a stabilizing element between the body tissue and body structure adjacent the incision; and with the stabilizing element deployed, pulling the tubular body to retract the body tissue from the body structures. With the body tissue retracted, the adjacent body structures can be more easily visualized.

In another aspect, the method contemplates the stabilizing elements includes forming a space between the stabilizing elements and a lower edge of the tubular body sufficient for ingress of the body tissue into the space. This aspect facilitates advancement of a needle tip carrying a suture therethrough to be captured by the stabilizing element. Thus, a further aspect of the inventive method comprises advancing the needle tip and suture from the tubular body, through body tissue between the tubular body and toward the stabilizing element, and then capturing the needle tip with the suture at a free end of the stabilizing element. Once captured, the stabilizing elements can be moved to a removal position with the needle tip captured at the free end thereof.

The tubular body is withdrawn from the incision with the needle tip captured so that the suture forms a ligature through the body tissue at the incision.

It is one object of the present invention to provide a closure device that facilitates the closure of an incision through body tissue of a patient. Another object of the invention is achieved by features that allow for a minimal number of steps to introduce and operate the closure device to pass sutures through the body tissue.

One particular benefit of the invention is that it is readily usable where the tissue layers are relatively deep. Another benefit is that the closure device facilitates closing the incision subcutaneously. A further benefit of the invention is that multiple sutures, preferably two, may be passed through the tissue and withdrawn simultaneously to form closure ligatures. Yet another benefit of the present closure device is that the device protects abdominal structures from the suturing needle as all suturing activities occur between the device wings and the fascia. Other objects and benefits of the invention will become apparent upon consideration of the following written description and accompanying figures.

DESCRIPTION OF THE FIGURES

FIGS. 9a-b are side views of a suture closure tool according to a further embodiment of the invention, shown with the stabilizing elements in their insertion position.

FIG. 17 is a side view of a suture closure tool according to a further embodiment of the invention using a substantially continuous needle.

FIG. 18 is a top view of the closure tool shown in FIG. 17.

FIG. 19 is a side view of a suture closure tool modified from the embodiment shown in FIG. 17.

DESCRIPTION OF THE PREFERRED EMBODIMENTS

Figure 1:
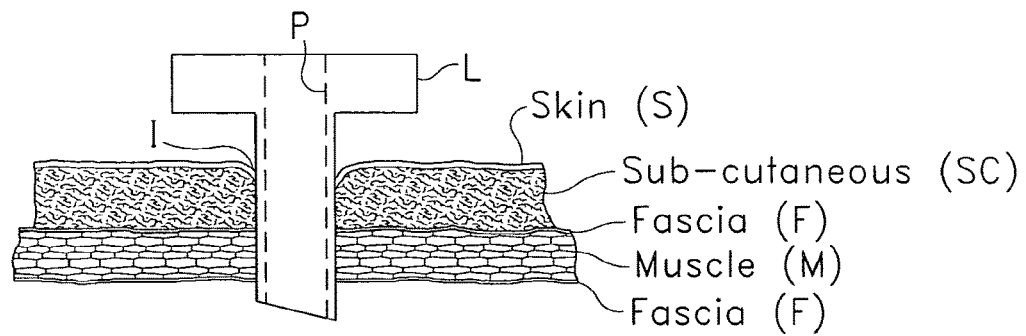
FIG. 1 is a side representation of a laparoscopic port extended through an incision in a patient.

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

One phase of a typical laparoscopic procedure is shown in FIG. 1. In particular, a laparoscopic tool L defining a port P is extended into a small incision I. The incision passes through multiple tissue layers for access to the patient's abdomen, for instance. Thus, the laparoscopic tool extends through the skin, subcutaneous and muscle layers, as well as the various fascia layers to provide access to the insufflated abdomen. The laparoscopic port P provides a point of entry for a surgical tool, visualization instrumentation and other tools and instruments well known in the field of laparoscopic surgery.

Figure 2:
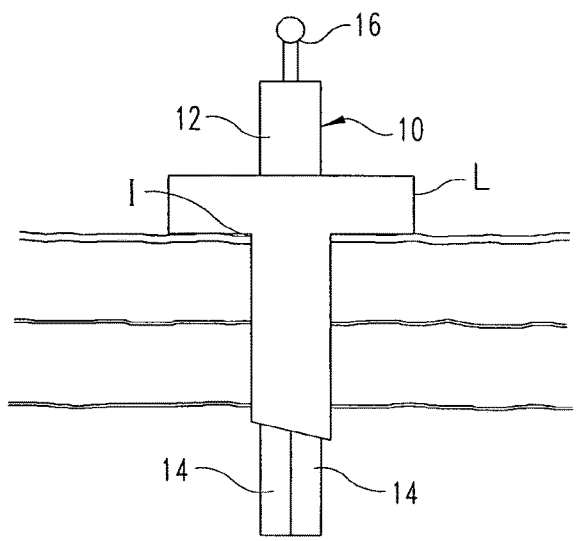
FIG. 2 is a side representation of the laparoscopic port of FIG. 1 with a suture closure tool of one embodiment of the invention extending therethrough.
Figure 4:
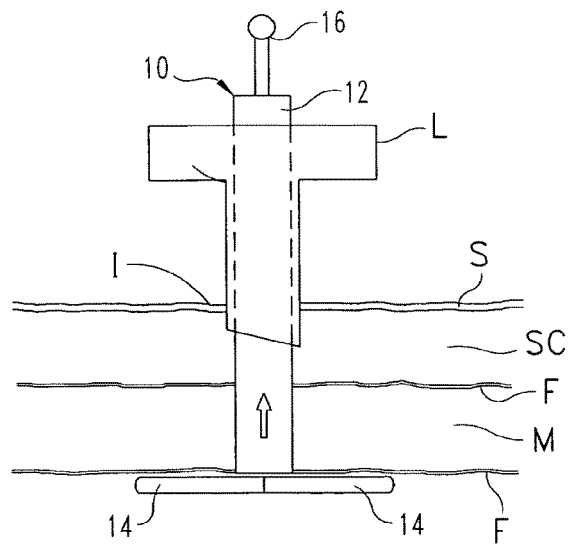
FIG. 4 is a side representation of the port and closure tool shown in FIG. 3 with stabilizing elements of the closure tool depicted in their operative position.

Naturally, once the laparoscopic tool L is removed and the procedure complete, the incision I must be closed. The present invention contemplates a closure tool 10 that is configured in one embodiment to pass through either the laparoscopic port P, as shown in FIG. 2, or through the port incision I. The tool 10 generally includes an upper cannula 12 and stabilizer elements 14 that are disposed at the distal end of the cannula 12. An actuator 16 is operable to deploy the stabilizer elements 14 into their operative position, as shown in FIG. 4 once the laparoscopic tool L has been withdrawn or removed. In this operative position, the stabilizer elements 14 are displaced outwardly beyond the confines of either the cannula 12 or the laparoscopic tool L. In this position, the entire closure tool 10 can be pulled upward so that the stabilizer elements 14 exert pressure on the innermost fascia F and slightly compress the tissue layers around the incision I.

The stabilizer elements 14 provide the ability for the surgeon to lift the abdominal wall to clear adjacent organs to decrease the risk of injury to adjacent organs. In certain procedures, the abdominal wall may be lifted as much as about 2.0 cm. or more which is useful to improve visibility or surgical tool access. This feature is particularly helpful for procedures involving patients with thick subcutaneous tissue layers, such as obese patients. In another beneficial attribute, the slight compression of the tissue layers caused by pulling the abdominal wall upward using the stabilizer elements 14 may facilitate passage of a suture needle through the tissue.

Figure 3:
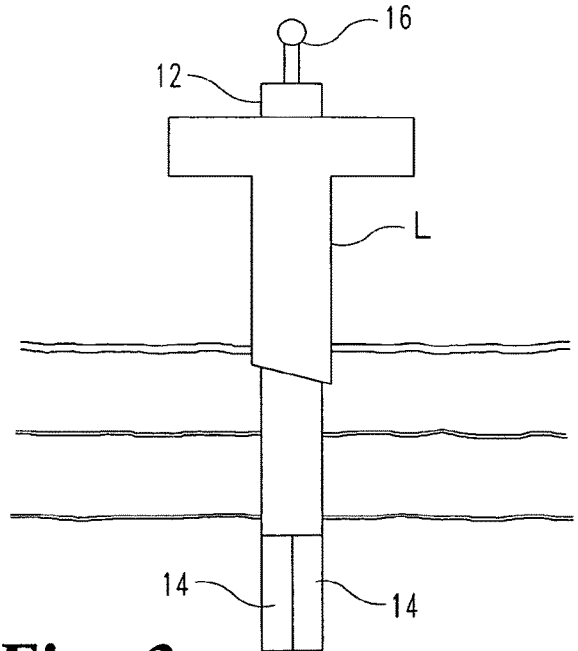
FIG. 3 is a side representation of the port and closure tool shown in FIG. 2, with the laparoscopic port partially withdrawn.

The present invention contemplates that the stabilizer elements 14 are pivotably mounted to the upper cannula 12 so that the elements can pivot from their insertion position, as represented in FIGS. 2-3, and their operable position, as shown in FIG. 4. In one embodiment, the elements 14 may be situated at substantially right angles relative to the insertion direction, as depicted in FIG. 4. Alternatively, the elements 14 may be at a non-perpendicular angle in their operable position (see, for instance, FIG. 13a). In the embodiment shown in FIG. 5, the stabilizer elements 14 are mounted to the cannula 12 at a pivot mount 18. In this embodiment, the pivot mount is carried at the end of an arm 20 that preferably spans the diameter or across the width of the cannula 12.

The actuator 16 is slidably disposed within the upper cannula 12 and is connected to the stabilizer elements by a pair of pull wires 22. The pull wires 22 are engaged to the stabilizer elements 14 at a point 24 remote from the pivot mount 18 so that an upward force exerted on the pull wires 22 by the actuator 16 will cause the elements to pivot about the pivot mount. As the stabilizer elements pivot, they swing upward, as indicated by the directional arrows in FIG. 5. The distal end of the cannula 12 can define opposing openings 25 to receive the inboard portion of the stabilizer elements when they are in their operative position.

Figure 5:
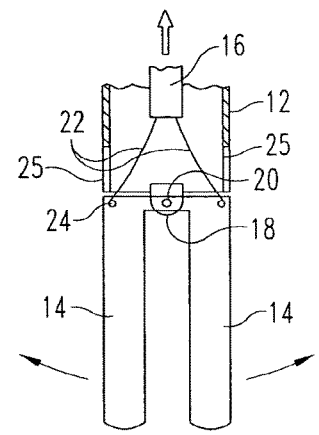
FIG. 5 is an enlarged partial cross-sectional view of the distal end of the closure tool shown in FIGS. 2-4, with the stabilizing elements shown in their insertion/retraction position.

In the position shown in FIG. 5, the stabilizer elements can be inserted into the incision I, either directly or through the laparoscopic tool P. In addition, the closure tool 10 can also be removed with the stabilizer elements 14 in that position. Thus, the present invention contemplates that the stabilizer elements can be returned to their aligned position depicted in FIG. 5. In one specific embodiment, a torsion spring (not shown) can be disposed within the pivot mount 18 to bias the stabilizer elements 14 to their insertion position shown in FIG. 5. When it is desired to deploy the stabilizer elements, pulling the actuator 16 exerts a moment on the pivoted end of the elements against the biasing force of the torsion spring. When it is desired to remove the tool 10 from the surgical site, the actuator 16 can be depressed relative to the cannula 12 so that the torsion force of the spring naturally tends to pivot the stabilizer elements 14 to the insertion/removal position.

Figure 6:
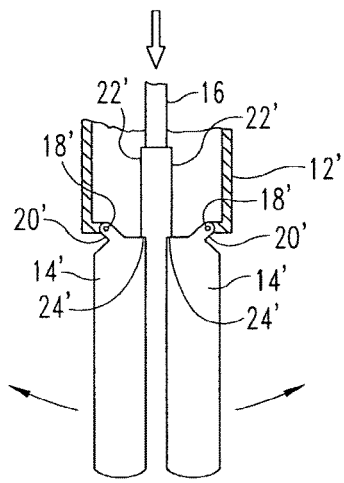
FIG. 6 is an enlarged partial cross-sectional view of stabilizing elements in an alternative embodiment of the invention.

In an alternative embodiment, shown in FIG. 6, the stabilizer elements 14' are pivotably mounted by pivot arms 20' to pivot mounts 18' defined on the interior of the upper cannula 12'. The actuator 16 is connected by push rods 22' to the stabilizer elements at mounting points 24'. In this embodiment, the push rods 22' are generally rigid but pivotably mounted at their ends to the actuator 16 and the mounting points 24'. When the actuator 16 is pushed downward, as indicated by the arrow, the stabilizer elements 14' swing outward into the operative position shown in FIG. 4. When it is desired to retract the elements 14', the actuator is pulled upward, which in turn pivots the elements 14' in the counter-direction until they are aligned with the cannula 12', as shown in FIG. 6.

Figure 7A:
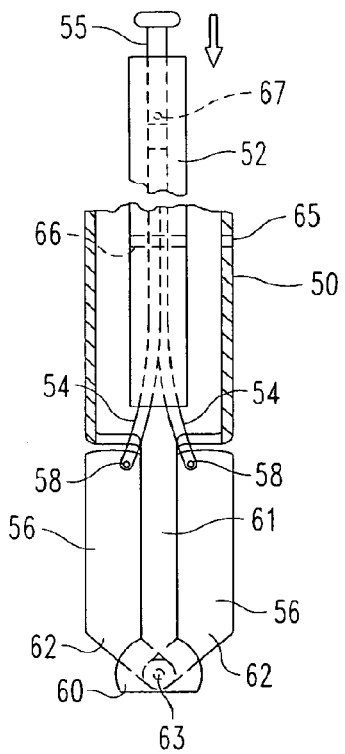
FIGS. 7a-c are sequential representations of the deployment of stabilizing elements in yet another embodiment of the invention.
Figure 7B:
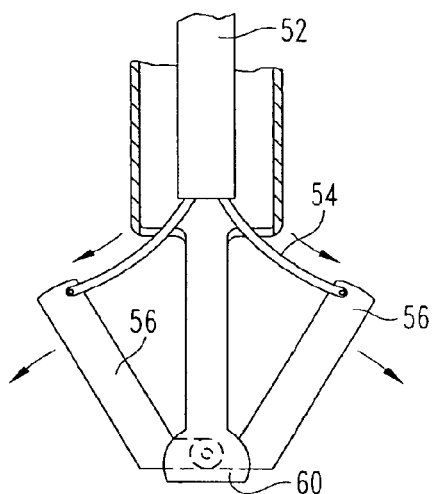
Figure 7C:
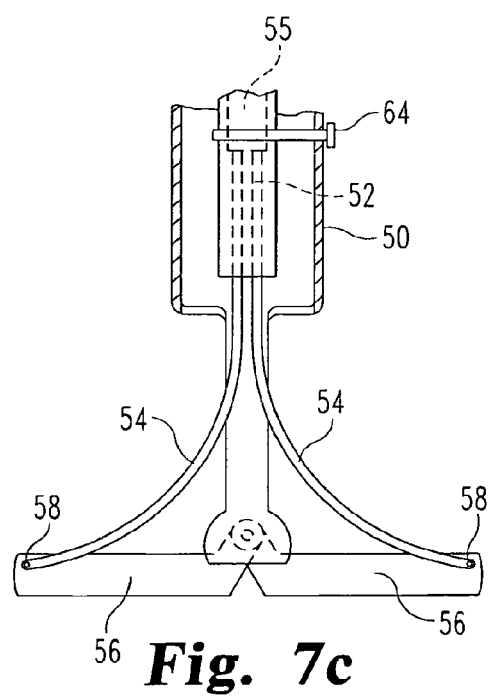

A related concept is depicted in FIGS. 7a-c. In this embodiment, the cannula 50 carries a tube 52 that supports an actuator plunger 55. The proximal end of the tube 52 may be flared (not shown) to provide a finger gripping location to facilitate depressing the plunger 55 and to provide a purchase point to pull or retract the tool 50, as described herein. The plunger is connected to actuator wires 54 that are fixed at a mounting point 58 to each of the stabilizer elements 56. The stabilizer elements 56 are pivotably mounted to a pivot mount 60 that extends from the base of the cannula 50. In the specific embodiment, the pivot mount 60 is situated between opposite legs 61 projecting from the cannula. The stabilizer elements 56 include pivot arms 62 that are mounted on an axle 63 that extends between and is supported by the legs 61 at the pivot mount.

The stabilizer elements 56 start in their retracted position shown in FIG. 7a to permit insertion through the incision. Once the elements 56 are visualized beneath the tissue layers, the actuator plunger 55 is depressed so that the actuator wires 54 push the stabilizer elements 56 outward about the pivot mount 60, as shown in FIG. 7b. In this embodiment, the actuator wires are bendable but stiff enough to permit transmission of an axial force from the plunger 55 through the wires against the free ends of the stabilizer elements 56.

As the plunger is pushed further, the wires push the stabilizer elements 56 until they reach their deployed position shown in FIG. 7c. In this position, a locking pin 64 can be extended through aligned pin bores 65, 66 and 67 in the upper cannula 50, tube 52 and actuator plunger 55, respectively. The pin thus holds the actuator, and therefore the stabilizer elements, in the position shown in FIG. 7c so that the stabilizer elements can be pulled upward into the tissue, as described above. When it is desired to remove the closure tool, the locking pin 64 is removed and the actuator plunger 55 is either pushed further downward, in which case the elements 56 pivot downwardly, or the plunger is pulled back, in which case the elements 56 pivot upward back to their original position shown in FIG. 7a. It can be appreciated that in this embodiment, as well as in the embodiment of FIG. 6, no torsion spring or biasing element is required.

Figure 8:
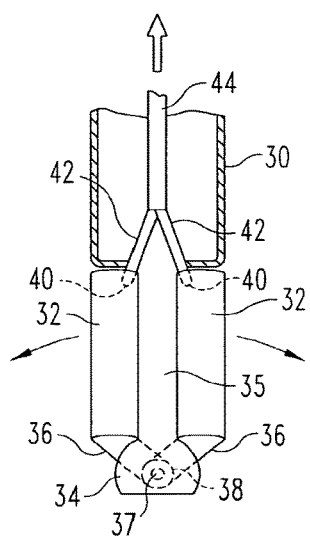
FIG. 8 is an enlarged partial cross-sectional view of stabilizing elements in another embodiment of the invention.

An alternative embodiment that does utilize a biasing element is shown in FIG. 8. In this embodiment, a cannula 30 includes downwardly projecting legs 35 that support a pivot mount 34 for the stabilizer elements 32. The elements include pivot arms 36 that are supported on an axle 37 supported by the legs 35. A torsion spring 38 may be disposed between the pivot arms 36 of the two stabilizer elements 32, or each element can include a torsion spring disposed between it and the pivot mount. The torsion spring 38 is configured to bias the stabilizer elements 32 to their deployed position, as shown in FIG. 4.

In this embodiment, the stabilizer elements 32 are held in their insertion position, shown in FIG. 8, by locking wires 42 that fit within recesses 40 in the tips of the elements. The locking wires 42 are connected to an actuator 44 that may be retracted or moved upwardly to release the locking wires 42 from the recesses 40. Once released, the torsion spring 38 causes the stabilizer elements 32 to automatically pivot about the pivot mount 34. A movable limit stop may be incorporated into the pivot mount 34 to hold the stabilizer elements in the deployed position. These limit stops may then be removed to allow the elements to continue to pivot until they are in line with the cannula 30 to permit removal of the closure tool.

Another embodiment of the invention that utilizes s torsion spring at the pivot mount is depicted in FIGS. 9-12. The closure tool 70 includes a body or cannula 71 that is sized to fit within the incision or through the laparoscopic tool P. The cannula 71 is formed by an annular wall 72 (FIG. 12c) that is preferably formed or molded in a medical grade material. In one specific embodiment, the body 71, as well as most of the components of the closure tool 70, is formed of an inexpensive, readily disposable material, such as a medical grade plastic.

The closure tool 70 includes stabilizer elements 74 that are configured to bear against the inner fascia of the patient's tissue from within the insufflated surgical site and to provide pressure to compress the tissue during suture insertion. The stabilizer elements 74 are further configured to move from the compact insertion position shown in FIGS. 9a-b, to the extended operating position shown in FIGS. 10a-b, to the removal position depicted in FIGS. 12a-b. An actuator 76 is provided to accomplish moving the stabilizer elements between the three positions.

In the illustrated embodiment, the stabilizer elements are supported on the cannula 71 at a pivot mount 78. The pivot mount 78 is offset from the cannula by support legs 79. An axle 80 extends between the legs 79 to support the stabilizer elements. Each stabilizer element 74 includes a wing 82 that is supported on a pivot hub 84 defining an axle bore 85 (FIG. 11a) for mounting on the axle 80. In this preferred embodiment, a torsion spring 88 is disposed on the axle 80 between the two pivot hubs 84. The ends of the torsion spring 88 may be embedded or locked within the hubs in a known manner that is sufficient to reliably rotate the two wings 82 of the stabilizer elements 74. The torsion spring 88 is calibrated to fully rotate both wings to the removal position shown in FIGS. 12a-b, in the absence of any restraint against rotation of the wings. Although a single torsion spring 88 is provided between the two hubs 84, each hub can be provided with its own torsion spring that operates between the hub and a corresponding support leg 79. However, a single torsion spring may be preferred for ease of assembly and reduced space requirements.

The actuator 76 restrains the two wings 82 from pivoting under the influence of the torsion spring 88. In the illustrated embodiment, the actuator 76 includes an actuator bar 90 that passes diametrically through the cannula 71, and more specifically through opposite actuator channels 98 defined in the cannula wall 72. Knobs 91 at the opposite ends of the bar 90 retain the bar within the channels 98 and provide for manual engagement to operate the actuator 76. Preferably, the knobs 91 are grasped between the thumb and forefinger to manipulate the actuator bar 90 within the two channels 98.

A pair of flexible cables 93 are fastened at one end to the actuator bar 90 and at the opposite end to the spool hub 95 of a corresponding pivoting wing 82. The cables 93 are configured to be wound around a respective spool hub 95 when the stabilizer elements 74 are rotated from their insertion position shown in FIGS. 9a-b to their removal position illustrated in FIGS. 12a-b. In other words, the torsion spring 88 is operable to rotate each pivot hub 84 and associated spool hub 95 to gradually wind the corresponding flexible cable onto the spool.

Of course, when the flexible cables 93 are held in position by the actuator bar 90, the cables resist further rotation of the pivoting wings 82. Thus, when the actuator bar 90 is situated at the top of the actuator channel within the insertion detent 100, the flexible cables 93 are taut and work against the torsion spring 88 to hold the wings 82 in their insertion position shown in FIGS. 9a-b. When it is desired to move the wings to their operative position of FIGS. 10a-b, the actuator bar 90 is manually moved from the detent 100 to the detent 102, thereby moving the cables toward the spool hubs 95. The torsion spring rotates the spool hubs to take up the slack in the cables 93, and at the same time pivot the wings 82 to the operative position. Finally, when it is necessary to remove the closure tool 70, the actuator bar 90 is manually moved from the detent 102 to the detent 104 at the end of the actuator channel 98. The slack in the cables 93 is again taken up by rotation of the spool hubs 95 under the influence of the torsion spring 88. When the closure tool 70 has been removed, the stabilizer elements 74 can be returned to their initial closed position (FIGS. 9a-b) by pulling the actuator bar up the channel 98 to the first detent 100. This movement unwinds the cables 93 from the corresponding spool hubs 95 causing the hubs to rotate against the torsion springs.

In order to prevent inadvertent movement of the actuator bar 90, the actuator channel 98 includes a ramp portion 101 between the first detent 100 and the second detent 102, as well as a comparable ramp portion 103 between the second and third detents 102, 104, respectively. The ramp portions are inclined upward or away from the first and second detents so that the actuator bar 90 must be pulled upward to dislodge the bar from the corresponding detent.

Figure 10A:
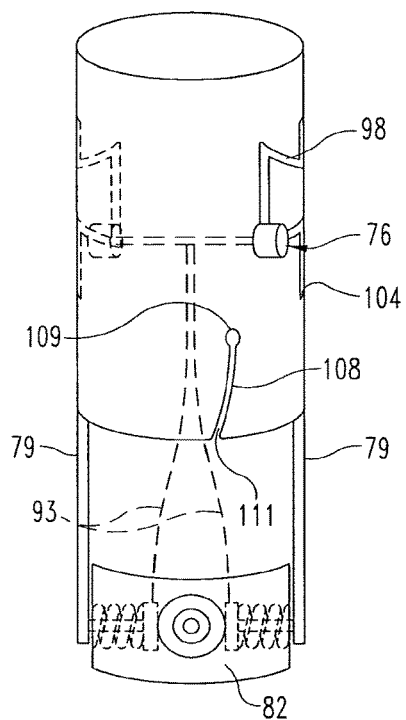
FIGS. 10a-b are side views of the suture closure tool depicted in FIGS. 9a-b, shown with the stabilizing elements in their operative position.
Figure 10B:
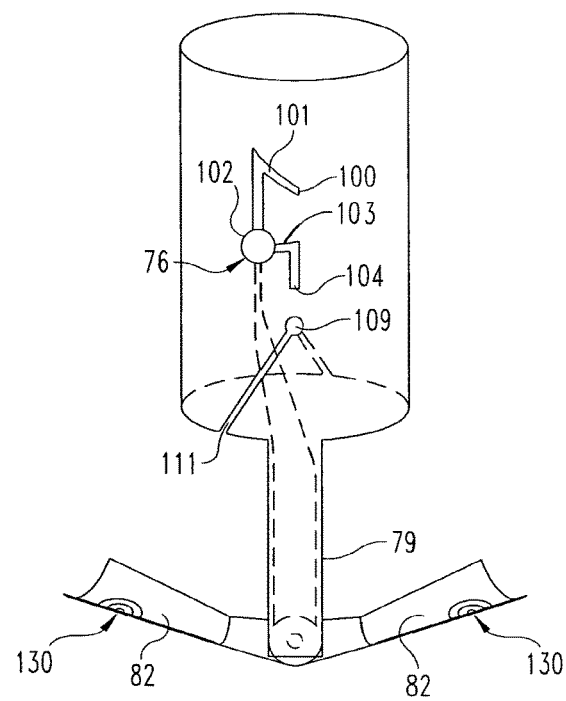
Figure 12A:
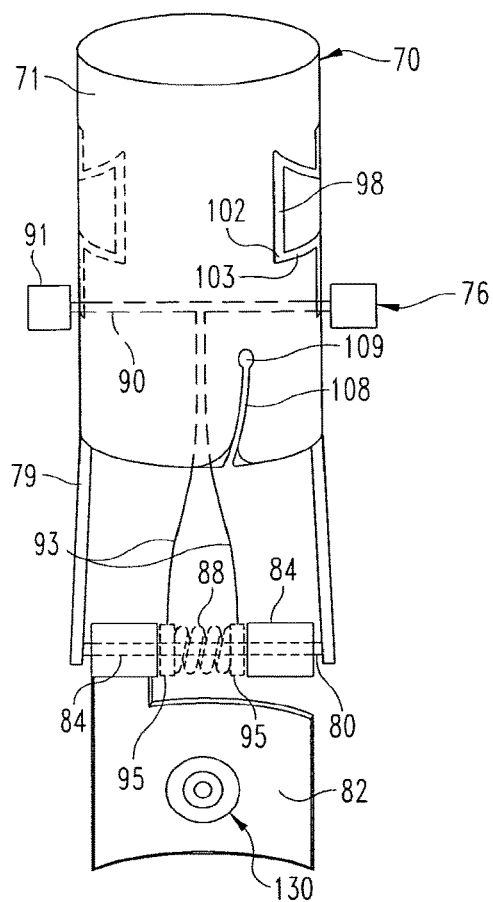
FIGS. 12a-b are side views of the suture closure tool depicted in FIGS. 9a-b, 10a-b, with the stabilizing elements in their removal position.
Figure 12B:
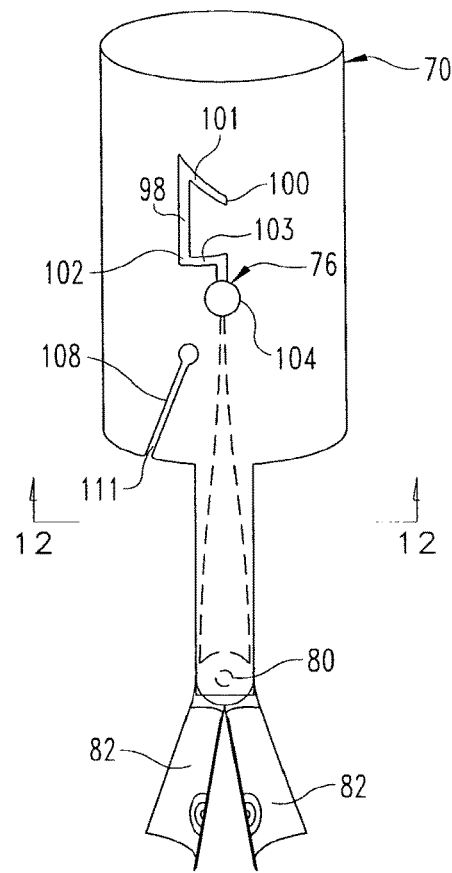
Figure 12C:
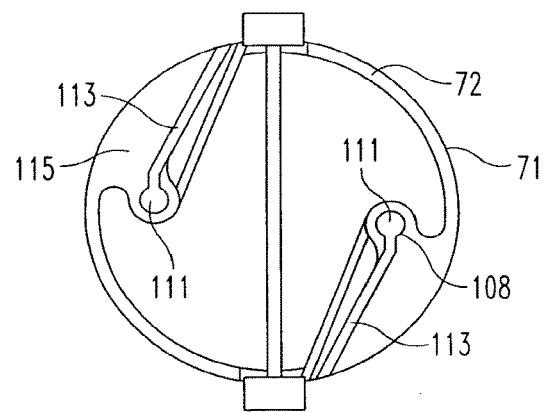
FIG. 12c is a bottom view of the suture closure tool shown in FIG. 12b, as viewed in the direction of the arrows.

As thus far described, the closure tool 70 includes means for stabilizing the tool relative to the tissue and incision. Moreover, the stabilizer elements 74 provide means for lifting the tissue layers away from intra-peritoneal structures. As explained above, lifting the tissues away from organs, for instance, may help in visualizing the surgical site as well as help in providing clear access to internal body structures. The stabilizer elements also provide some compression of the tissue around the incision, which can facilitate passage of a suture needle through the tissue. The closure tool thus provides means for directing a suture through the tissue and capturing the suture so that when the tool is removed the ends of the suture are accessible to tie off and close the incision. Thus, in accordance with one aspect of the illustrated embodiment, the cannula wall 72 defines a pair of diametrically opposite needle guide channels 108, as best seen in FIGS. 10*b* and 12*c*. The guide channels are arranged so that a straight needle passing through the channels will approach the tip of each pivoting wing 82 when the wings are in their operative position shown in FIG. 10*b*.

The guide channels define an entry opening 109 at the side of the cannula 71 that is positioned to reside sufficiently above the skin of the patient when the closure tool 70 is in its operative position. The opening 109 can be conical to facilitate introduction of a suture needle into the channel. Each channel 108 further defines an exit opening 111 at the base of the cannula and aligned with the top of the corresponding pivoting wing 82 in the operative position of FIG. 10*b*. It is understood that the guide channels 108 and their corresponding entry and exit openings are aligned to avoid encroachment with the other components of the closure tool 70. The exit openings are also preferably aligned so that a suture needle exiting the channels will contact the fascia of the incision below the skin layer. Preferably, the exit openings 111 are arranged so that the suture needle will first penetrate the subcutaneous tissue SC (FIG. 1). With this preferred arrangement, the support legs 79 for the pivot mount 78 supporting the extended wings 82 have a length approximately equal to the nominal thickness of the muscle layer M and fascia F beneath the subcutaneous tissue SC. It can be appreciated that when the closure tool 70 is in its operative position, a portion of the cannula 71 is disposed within the upper portion of the incision I.

In another aspect of the needle guide channels 108 define a suture slot 113 (FIG. 12*c*) along the length of each channel. The suture slot 113 is narrower than a suture needle, but sufficiently wide to allow a suture to pass through as the suture needle is advanced along the channel. The suture slot 113 thus facilitates accessing the free ends of the suture once the suture has passed through the tissue layers and the closure tool removed from the incision.

As indicated above, the cannula 71 is preferably molded from a medical grade plastic. With this construction, the needle guide channels 108 can be integrally formed with the wall 72 with a web 115 spanning the space between the wall and the channels. The webs 115 support the guide channels so that they hold their position relative to the extended pivoting wings 82.

Figure 13A:
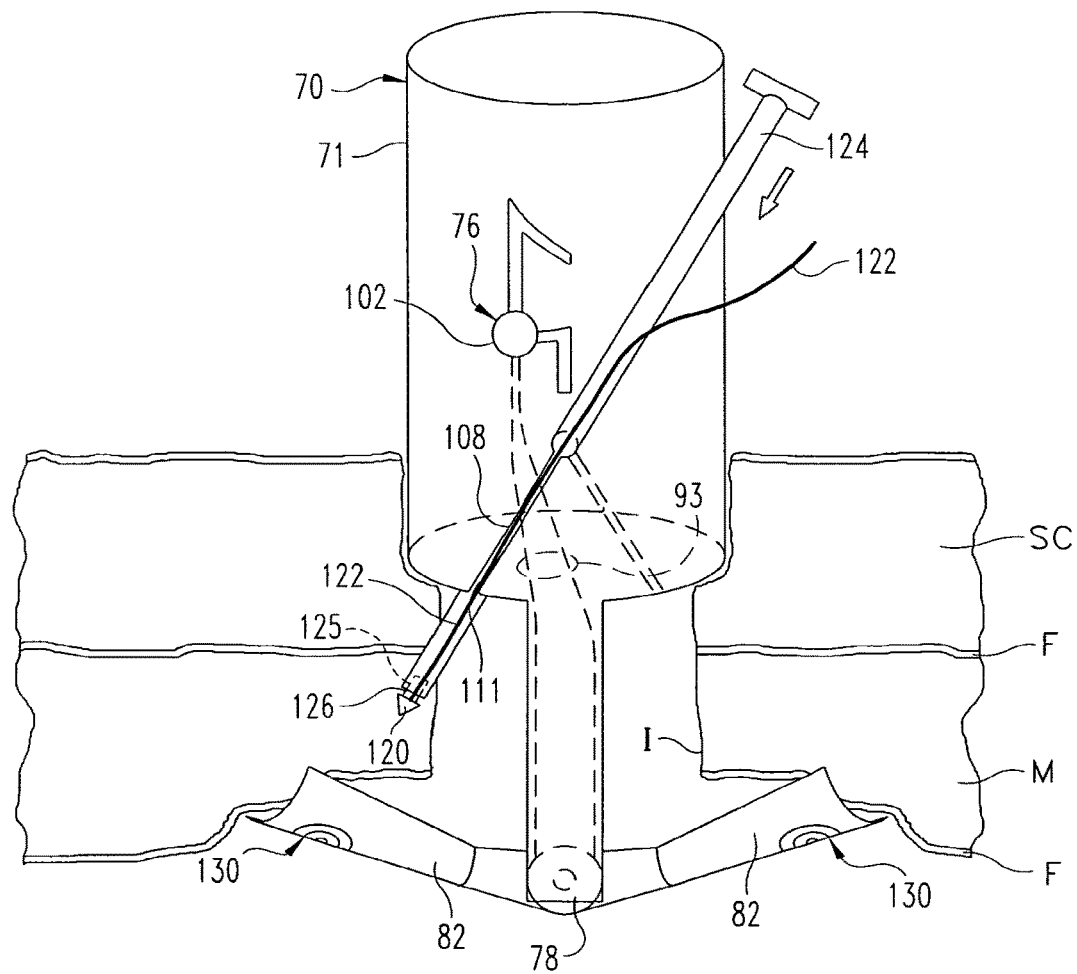
FIGS. 13a-e are side views of the suture closure tool shown in FIGS. 9-12 in use to pass a suture through the patient tissue to close the incision.

In accordance with a further feature of the invention, each suture 122 is carried by a needle tip 120, as shown in FIG. 13*a*. The needle tip 120 is essentially simply the tip of a suture needle, absent the needle shaft. The suture 122 is fastened to or held by the needle tip in a known manner, such as by crimping the suture within a slot formed in the tip. The suture must be fastened to the needle tip in a manner that prevents its separation from the needle tip 120 during use of the closure tool 70. It is understood that once the ligature loop has been completed at the incision the suture can be cut at the needle tip, leaving a free end of the suture.

Since the suture is carried only by a needle tip, the invention contemplates a needle driver 124 that carries and propels the needle tip through the guide channels 108 and through the tissue layers. The needle driver 124 can be provided with a bore 125 to removably receive a base portion 126 of the needle tip. Other methods for removably engaging the needle tip 120 to the needle driver 124 are contemplated provided that the driver can be easily removed from the needle tip once the needle tip and suture has been passed through the tissue layers.

The closure tool 70 thus provides means for directing a suture needle carrying a suture toward the extended wings 82. The wings 82 are themselves provided with means for capturing the suture needle, and ultimately one end of the suture. In one embodiment, the tip of each pivoting wing 82 includes a capturing device 130, as shown in FIG. 1*a*, that is configured to capture the needle tip 120 and hold it from retrograde movement as the wings are pivoted to their removal position of FIGS. 12*a-b* and as the closure tool 70 is removed from the incision. In this embodiment, the capturing device includes a guide ring 132 that is configured to guide the needle tip toward the center of the capturing device 130. The device includes a resilient flap structure 134 at the center of the guide ring with a center opening 136 to receive the point of the needle tip. As the needle tip is advanced toward the capturing device, the guide ring aligns the point of the needle tip with the center opening 136. As the needle tip is pushed further it pushes past the resilient flaps which separate slightly but collapse about the base portion 126 of the needle tip once the tip has passed completely through the center opening. The guide ring is preferably slightly conical to direct the needle tip to the center opening even if the needle tip contacts the wing 82 slightly offset.

Figure 11A:
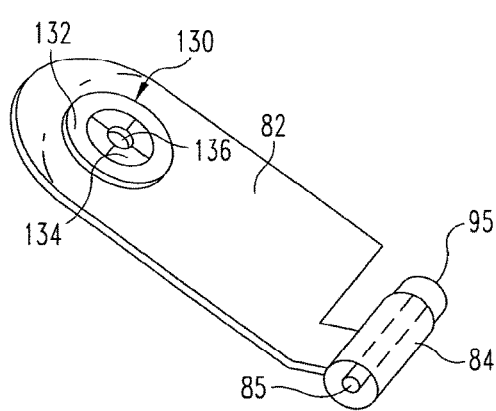
FIGS. 11a-b are enlarged perspective views of alternative embodiments of a tissue facing portion of a stabilizing element for use with any of the embodiments shown above.
Figure 11B:
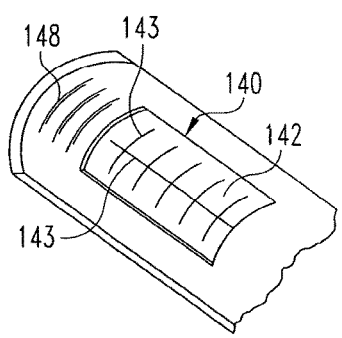

In an alternative embodiment, a capturing device 140 is provided as shown in FIG. 11*b* that is rectangular rather than circular in configuration. In this embodiment, the device includes a series of resilient flaps 142 with separation lines 143 providing areas in which the flaps can be separated for passage of the needle tip. These flaps 142 operate like the retention flap 134 described above to capture the needle tip and prevent its retrograde movement. In both embodiments of FIG. 1*a* and FIG. 11*b* the corresponding retention flaps hold the needle tip as the needle driver 124 is disengaged from the needle tip.

In certain embodiments, the tip of each pivoting wing 82 can be provided with a gripping feature, such as the ridges 148 depicted in FIG. 11*b*. This gripping feature may enhance the engagement of the stabilizer elements with the tissue as the wings are pulled upward to exert pressure on the body tissue. The material of the gripping feature, or ridges 148, must be capable of achieving solid purchase on the relatively slick surface of the fascia F. In one embodiment, the gripping feature is formed of a rubber or a SILASTIC® material.

Referring now to FIGS. 13a-e, the use of the closure tool 70 can be understood. In FIG. 13a, the wings 82 have been deployed into their operative position and the closure tool 70 pulled back to slightly compress the tissue layers. The closure tool is situated so that the exit opening of each needle guide channel 108 is aligned so that the needle tip 120 can pass directly into a portion of the subcutaneous tissue layer from inside the incision. The closure tool may be positioned to close the anterior fascia, the posterior fascia, or both.

The location of the body tissues shown in FIG. 13a illustrates a beneficial feature of the invention. In particular, in one aspect of the embodiment, the tubular body 71 of the closure tool 70 presents an outer diameter that is larger than the effective diameter of the incision I. Once the wings 82 are deployed, the body tissue at the incision wall tend to "flow" into the space between the tubular body 71 and the wings 82. A similar effect may be achieved if the tool 70 is deployed through a trocar or laparoscopic port P (FIG. 1) with a diameter greater than the effective diameter of the incision I. This tissue ingress enhances the ability to pierce the tissue layers with the needle tip 120, particularly for plural needle paths and suture sites.

With the closure tool so positioned, a needle tip 120 is loaded onto a needle driver 124, with the suture 122 fixed to the needle tip and the free end of the suture disposed outside the wound. The needle driver is then pushed toward the incision I to penetrate the tissue layers. As can be seen in FIG. 13a, the needle tip is aimed toward the capturing device 130 of the wing 82.

Figure 13B:
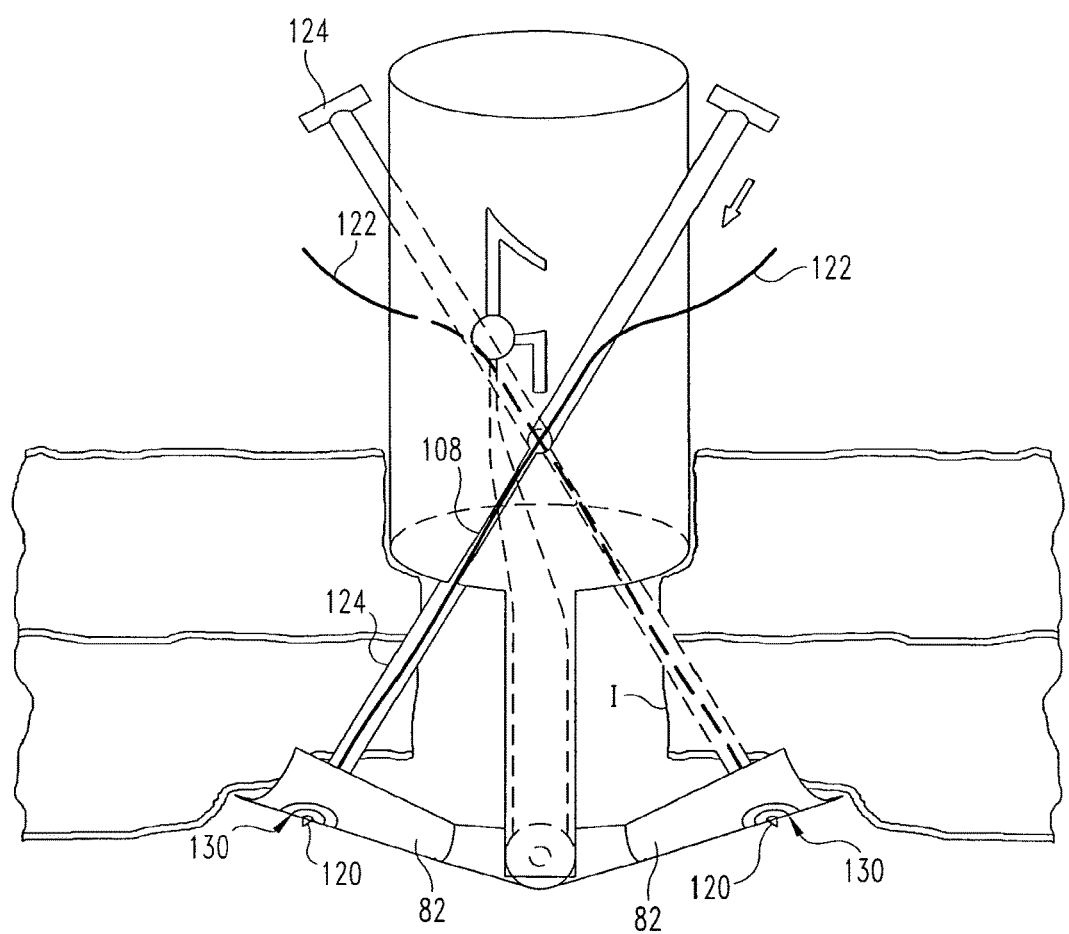

In FIG. 13b, the needle tip 120 has traversed the capturing device 120 and is held in position against its removal. The slight compression of the body tissue facilitates penetration of the needle tip so that the tip should be substantially aligned with the capturing device 130 when it reaches the wing 82. As reflected in FIG. 13b, a needle driver 124 is also used to drive a needle tip into the capturing device on the opposite wing 82 so that a suture 122 has been threaded through opposite sides of the incision I.

Figure 13C:
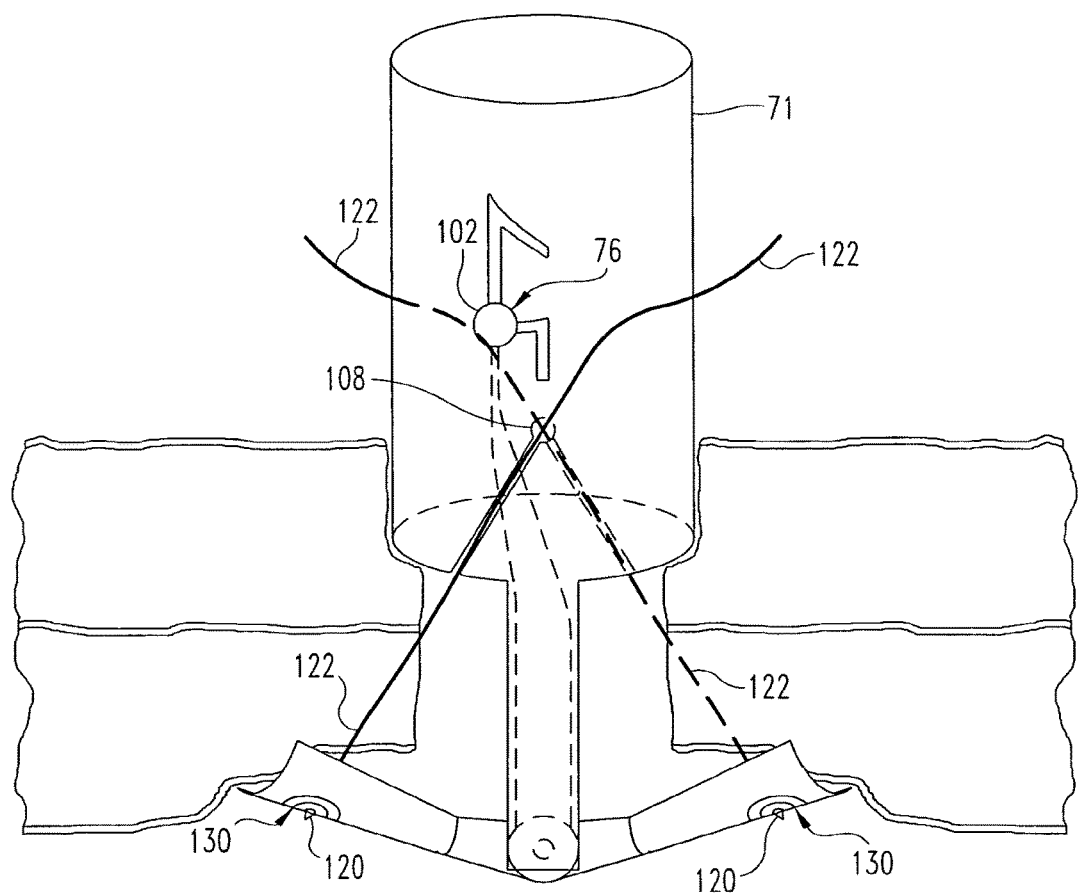

With both needle tips 120 retained in a corresponding capturing device 130, the corresponding needle driver 124 is separated from the needle tip, retracted and removed, as depicted in FIG. 13c. Each suture 122 may be temporarily positioned within the needle guide channels 108 or may be loose adjacent the cannula 71; however, the distal portion of the suture has been driven through the tissue around the incision.

Figure 13D:
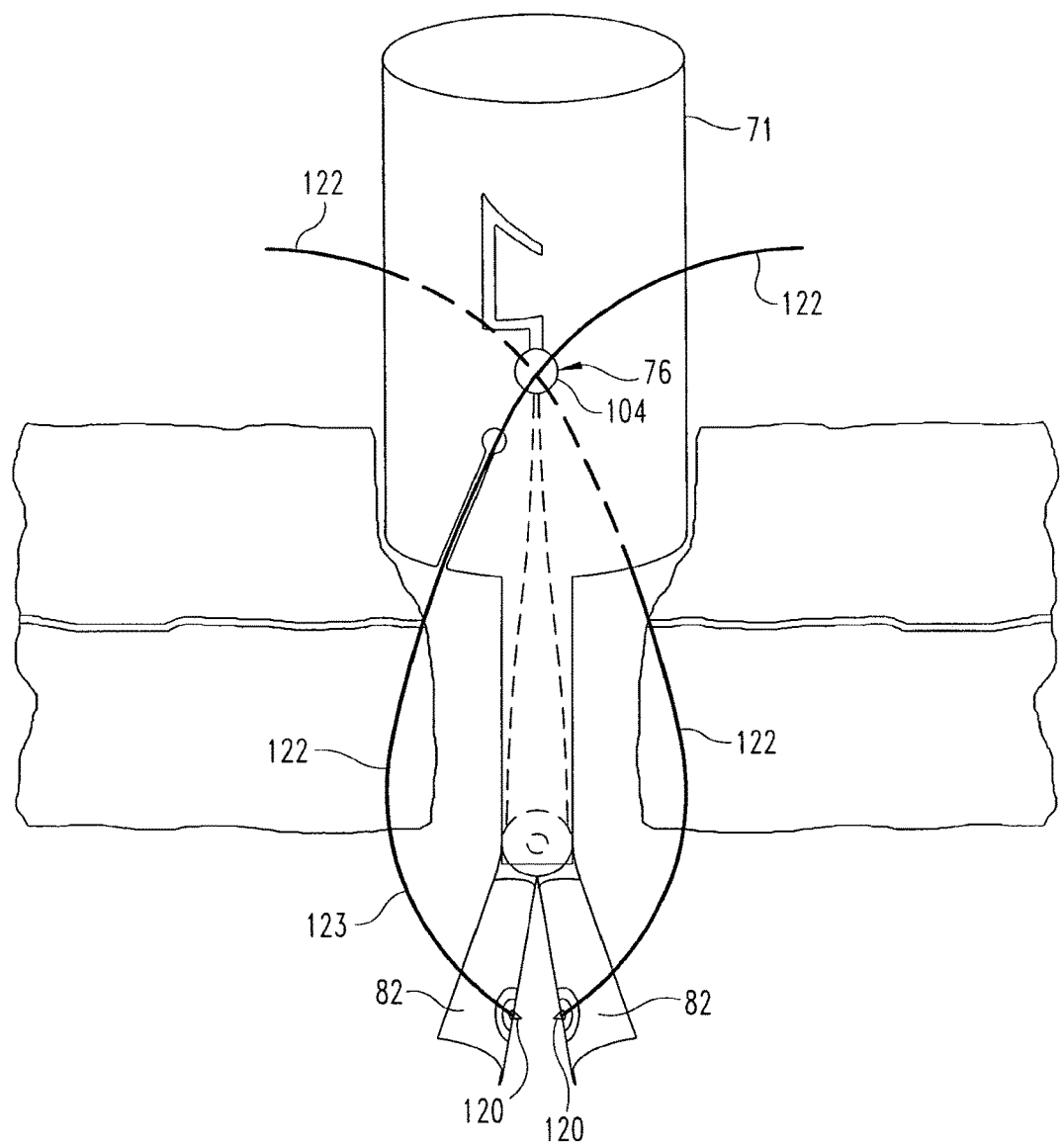

In the ensuing step, the wings are moved to their removal position, illustrated in FIG. 13d, in the manner described above. Specifically, the actuator 76 is moved to the lowest detent 104 so that the torsion spring can unwind and rotate the wings 82 until they are generally aligned with the longitudinal axis of the cannula 71. It is understood that as the wings rotate downwardly, they pull each suture 122 with them so that excess suture 123 is drawn through the closure site. At the same time, the cannula 71 may be pushed slightly into the incision to draw additional suture material into the site.

Figure 13E:
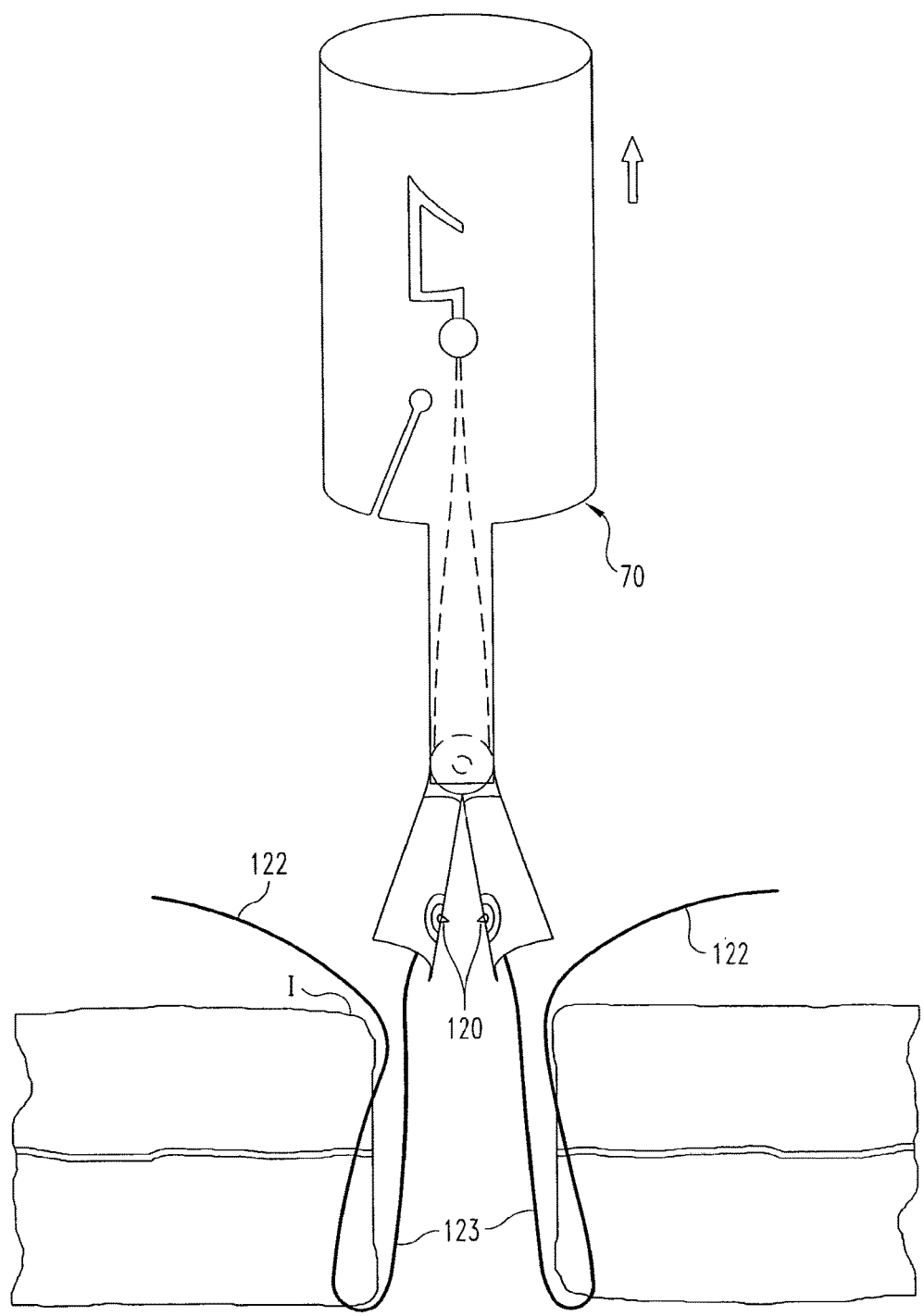

With the pivoting wings 82 in their removal position, the entire closure tool 70 may be removed from the incision, as shown in FIG. 13e. As the tool is withdrawn from the wound the excess suture 123 is pulled back through the incision to form a ligature loop. At this point, the suture can be cut at the needle tip 120 so that the free ends of each suture 122 are accessible outside the incision. The two sutures can then be tied off in a conventional manner to close the incision, and more particularly to close the fascial layers of the incision.

It can be appreciated that the closure tool 70 provides an easy and efficient mechanism for forming a subcutaneous ligature loop and closing an incision, especially in the abdomen. The device provides means for driving two sutures through the tissue without requiring direct vision of the process from within the body cavity. However, it is preferable that the process be visualized and that the position of the sutures be verified under direct vision before the opening is closed. In typical surgical practice, only two sutures are required to completely close an incision, so only a single operation of the tool 70 is required. However, if desired, additional sutures may be introduced at the incision. In a preferred embodiment, the closure tool 70 may be "reloaded" with a second set of needle tips 120 and sutures 122 and the tool repositioned within the incision I. In an alternative embodiment, an additional pre-loaded closure tool can be passed through the same incision with the sutures 122 in the position shown in FIG. 13e. The second closure tool placement may be aligned with the wings 82 at ninety degrees to the position of the wings of the first tool to pass two additional sutures at the ninety degree interval. The same procedure outlined in FIGS. 13a-e may be followed with this additional tool to provide four sutures to close the incision.

It is understood that in the preferred embodiment, each closure tool 70 is disposable and is intended to be discarded after each patient use once the sutures have been placed. Each closure tool is preferably provided pre-loaded—i.e., with each needle tip engaged to a corresponding needle driver, and each needle driver positioned within a corresponding needle guide channel. The needle driver can be configured to combine the driver for the suture needles on the opposite sides of the tool into a single driver so that only a single movement of the needle driver is necessary to penetrate the tissue and lodge each needle tip into a corresponding capturing device.

In the embodiment of FIGS. 9-13 a straight needle arrangement is utilized. In an alternative embodiment, a pre-curved needle or needle driver may be used. Thus, in one embodiment depicted in FIG. 14, a closure tool 150 includes a cannula 151 that defines a guide channel 152 for receiving a suture needle. The closure tool further includes stabilizer elements 156 that are connected to the cannula 151 by way of a pivot mount 158. As thus far described, the closure tool 150 can be constructed in a manner similar to the tool 70 described above. For instance, the stabilizer elements can include a torsion spring to bias the elements to their retraction position (see FIG. 13d). The tool 150 may also incorporate an actuator similar to the actuator 76 of the closure tool 70 (see FIG. 12a).

Figure 14:
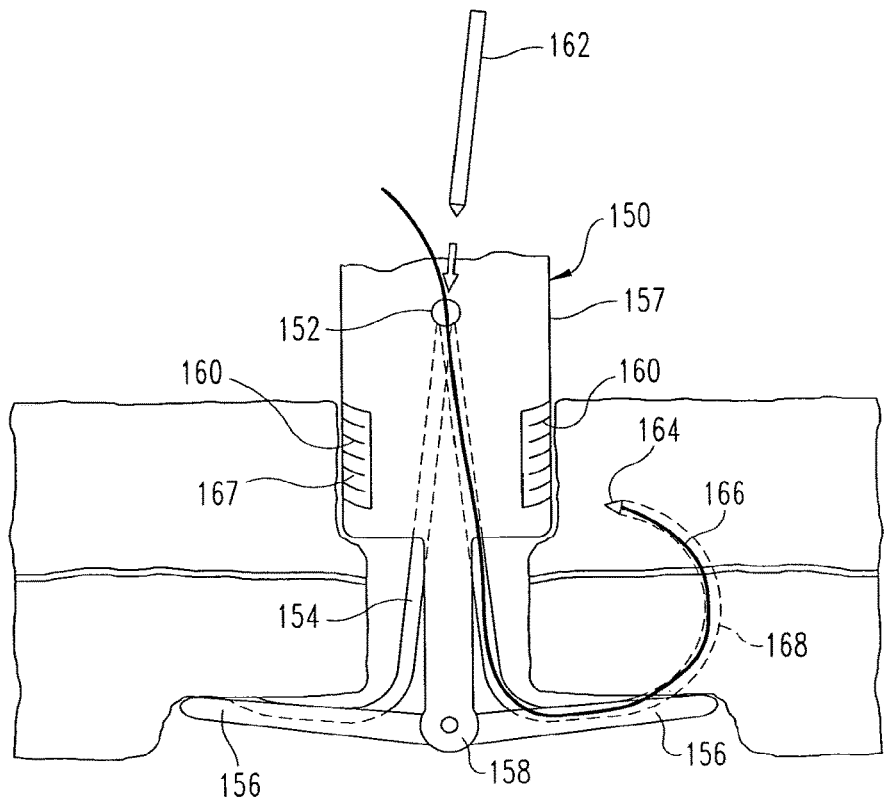
FIG. 14 is a side representation of an alternative suture closure tool using a pre-curved needle.

However, unlike the tool 70, the closure tool 150 incorporates a needle capture device 160 in the body of the cannula, as shown in FIG. 14. The capture device 160 may be configured similar to the capture devices 130 and 140 shown in FIGS. 11a and 11b, respectively. Thus, the capture device 160 may include resilient flaps 161 that separate as the needle tip passes into the device, and then collapse about the needle hub to hold the needle tip within the cannula 151.

The closure tool 150 further includes a guide tube 154 that extends from the guide channel to a corresponding pivoting wing 156. The wing supports the guide tube so that the end of the tube opens upward toward the tissue when the wing is in its operative position shown in FIG. 14. The guide tube is formed of a resilient, bendable material that can be essentially folded upon itself when the wing is in its closed or insertion position (see e.g. FIG. 9b), or fully unfolded when the wings are in their removal position (see e.g., FIG. 12b). In a specific embodiment, the guide tube is formed of a medical grade plastic.

Figure 15:
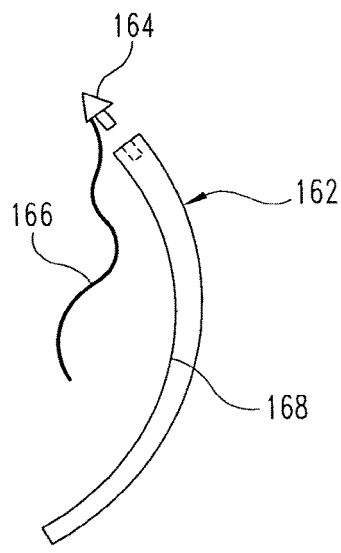
FIG. 15 is an enlarged view of a pre-curved needle for use with the closure tool shown in FIG. 14.

The guide channel 152 and guide tube 154 define a passageway along which a curved needle assembly 162 passes. The needle assembly includes a needle tip 164 to which is attached one end of a suture 166, as shown in FIG. 15. The needle tip and suture arrangement may be the same as the needle tip and suture described above. The needle assembly 162 further includes a pre-curved needle pusher 168. The needle pusher is formed of a material that can be pre-formed at a particular radius of curvature, as reflected in FIG. 15, but that is flexible enough to be initially straightened to pass through the guide channel 152. In accordance with one feature of this embodiment, the needle driver 168 flattens as it is pushed through the guide channel 152 and the upper portion of the guide tube 154. As the needle driver progresses along the guide tube it continues to follow the bend in that tube as well as the straight section of the guide tube along the length of the stabilizer element 156. Once the needle driver exits the guide tube 154 beneath the tissue layers, the driver starts to assume its pre-curved shape. As the needle driver and the needle tip it carries are pushed further into the tissue the driver continues to assume its pre-curved shape. The curved shape of the needle driver 168 is configured so that the needle tip 164 is guided toward the capturing device 160 on the outer surface of the cannula 151.

Figure 16:
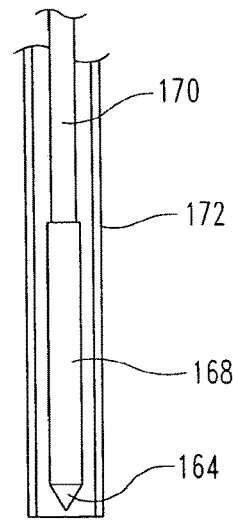
FIG. 16 is an enlarged view of a loading tube for introducing the pre-curved needle of FIG. 15 into the suture tool shown in FIG. 14.

It is understood that once the needle driver has pushed the needle tip into the capturing device, the tip is disengaged from the driver and the driver is retracted along the guide tube 154 and guide channel 152. It is contemplated that the needle driver is sufficiently long so that a proximal end of the driver is accessible outside the incision when the distal end of the driver carrying the needle tip has contacted the capturing device 160. In a specific embodiment, only the distal end of the needle driver is pre-curved since it is only necessary for the distal end of the driver to follow this pre-defined curvature to push the needle tip and suture through the tissue layers and arrive back at the cannula 151 of the closure tool 150. Thus, the needle driver can include a straight section 170 (FIG. 16) at the proximal portion of the driver.

In order to facilitate use of the pre-curved needle driver, the needle assembly 162 may be initially provided within a straight sheath 172. The sheath 172 may mate with the guide channel 152 to facilitate introduction of the pre-curved portion of the needle driver 168 into the guide channel.

With this embodiment, the guide channel 152 and guide tube 154 are continuous—i.e., they are not provided with a suture slot, like the slot 113 of the closure tool 70 described above. In this case, the suture 166 will pass through the channel 152 and tube 154 even when the closure tool 150 is removed form the incision. One end of the suture will be retained along with the needle tip 164 in the capturing device 160 as the tool is removed from the incision. The opposite end of the suture remains free because the suture will be pulled through the tissue as the captured end is pulled with the closure tool. Once the tool has been completely removed from the incision the suture can be cut at the end of the guide tube 154 and at the capturing device 160. The free ends of the sutures can be tied off in a conventional manner. As with the previous embodiments, once the sutures have been passed through the tissue layers and the closure tool retracted from the incision, the tool 150 can be discarded. Alternatively, a second set of pre-loaded pre-curved needle assemblies can be loaded into the tool and the tool re-introduced into the incision but rotated by ninety degrees relative to the sutures already in position.

In the embodiments of the closure tools described thus far, each suture is passed through tissue at one side of the incision and then drawn through the incision itself, as demonstrated by the ligature loops shown in FIG. 13e. In an alternative embodiment, a single suture passes through tissue layers on opposite sides of the incision, with the suture spanning the incision within the body cavity. Thus, in this embodiment, a closure tool 180 is provided with a continuous needle track 188 which guides a pre-curved needle 194 that is wholly contained within the tool 180, as shown in FIGS. 17-18.

As with the prior embodiments, the tool includes a pair of stabilizer elements 182 that can be rotated from a closed position to an operative position to a removal position. The actuators of the prior embodiments may be used to extend and retract the elements 182; however, in the illustrated embodiment of FIG. 17 a rack and pinion gear approach is utilized. In this embodiment, the pivot mounted end of the stabilizer elements 182 forms a pinion gear 183. A linear rack gear 185 extends through the closure tool 180 and includes rack threads that engage the pinion gear threads. An actuator knob 186 passes through a slot in the tool 180 so that the knob can be used to raise and lower the rack gear 185. As the rack gear is raised, it rotates the pinion gears 183 so that the stabilizer elements 182 swing away from the body of the tool 180. The slot (not shown) in the closure tool 180 can incorporate detents, like the actuator channel 98 of the tool 70 shown in FIG. 10 b, so that the actuator rack gear may be moved in indexed fashion between the three functional positions of the stabilizer elements 182.

In accordance with this embodiment of the invention, the closure tool 180 defines a continuous needle track 188 that winds around the circumference of the tool and along the length of the tool. The needle track is preferably configured to accommodate the pre-curved configuration of the needle 194. For instance, the needle track can gradually spiral up the length of one side of the tool 180 and spiral down the opposite side. The needle track traverses the body of the tool 180 at an exit opening 195 and an entrance opening 198 substantially opposite the exit opening. As shown in FIG. 17, the entrance opening 198 is larger than the exit opening and forms a taper to the needle track. This feature of the entrance opening helps guide the pre-curved needle 194 back into the tool 180 once it has passed through the tissue layers on both sides of the incision, as indicated by the dashed arrows in FIG. 17.

The needle track 188 is accessed through a pair of openings 190 and 192. The first opening 190 provides access to the needle 194 to engage a suture 191 to the needle. The needle can incorporate an eye through which the suture may be threaded in a known manner. Alternatively, the suture may be crimped onto the needle or otherwise fastened to the needle so that it can be drawn through the tissue layers with the needle. The opposite opening 192 allows access to the needle after the suture has been passed through the tissue and has been pulled through the needle track 188. The suture can be cut from the needle at this location before or after the closure tool has been removed from the incision. At a minimum, the second opening 192 allows for verification that the suture has been drawn through the tissue layers and is in position to close the incision.

In the preferred embodiment, the pre-curved needle 194 is curved so that it follows its pre-defined curvature as it exits the needle track 188 through the exit opening 195, as shown in FIG. 17. As the needle continues to curve through the tissue layers, it is self-directed to a guide slot 196 formed in the body of the tool 180. In the preferred embodiment, the guide slot includes an angled upper wall 197 that collects the needle tip even if it is slightly offset on its path through the tissue. The guide slot 196 is also open at its lower end so that a suture passing under the angled upper wall 197 is not trapped within the tool 180 when it is removed. At a minimum, the guide slot 196 is open at its lateral face so that the suture can be dislodged from the slot by a slight manipulation of the closure tool 180 as it is being removed from the incision.

Another feature of this embodiment is that the pre-curved needle is mechanically driven by a needle drive assembly 200. In one specific embodiment, the drive assembly 200 includes a pair of drive rollers 202 that are arranged to contact the needle 194 at opposite sides of the closure tool 180. An idler roller 204 is connected to an externally accessible crank 206. Rotation of the idler roller rotates the two drive rollers in opposite directions, with one roller 202 a propelling the needle up through needle track 188 and the other roller 202 b pushing the needle down through the track toward the exit opening 195. The rollers may be formed of a hard rubber that exhibits sufficient friction to propel the needle along the track. It can be appreciated that the needle track 188 defines openings at the rollers so the rollers can directly contact the needle within the track.

In accordance with this embodiment, the pre-curved needle has a length that permits at least one of the rollers 202 to be in driving contact with the needle 194 at all times. Since the pre-curved needle exist and re-enters the needle track, it must have enough length so that the needle tip encounters one of the rollers 202 a on its return to the tool 180 before the tail end of the needle loses contact with the other driver roller 202 b. At the same time, the needle track 188 is sized relative to the length of the needle so that the needle can be entirely contained within the closure tool 180 when the tool is inserted into or removed from the incision.

In an alternative embodiment, a drive assembly 212, configured like the drive assembly 200, can be situated at the base of a closure tool 210, as shown in FIG. 19. In this embodiment, the tool does not define a continuous needle track, but instead a discharge track 214 and a retrieval track 216. The drive assembly 212 is disposed between the two tracks to propel or pull a pre-curved needle 220 in the same circular path through the tissue layers at the opposite sides of the incision.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected.

For instance, in the various embodiments, a plunger, actuator knob and rotating crank have been disclosed for controlling the actuation of the stabilizer elements and for deploying the suture needles and needle tips. Other means for controlling the actuation and movement of these components are contemplated, including reusable devices that are configured to mate with the various closure tools. For instance, one alternative is to implement a squeeze handle to advance the suture needles through the tissue. In this alternative, the squeeze handle would include a fixed handle arm engaged to the tubular body of the closure tool and a movable handle arm connected to the needle driver in a suitable manner. For example, the movable handle arm may be connected to an end of the needle driver 124 shown in FIG. 13a through an appropriate linkage so that manually squeezing the handle drives the needle tip and suture the appropriate distance through the tissue.

As a further alternative, the actuation of the stabilizer elements may be initiated by a manual trigger through a spring-biased element adapted to extend the stabilizer wings to their operative position. Preferably, the trigger actuation for the stabilizer elements is combined with the squeeze handle actuation for the suture needle driver to provide single-handed operation of the closure tool. Since the closure tool is preferably disposable, the trigger and squeeze handle actuators may be provided separately with means for engaging the actuators to the closure tool. After each use, the separate actuator device would be cleaned and sterilized for use in another procedure.

In a further modification, the closure tools may incorporate one or more stabilizer elements or wings, with an appropriate number of needle guide channels. Alternatively, a single stabilizer wing may be configured to rotate relative to the tubular body of the closure tool to align with a plurality of needle guide channels disposed around the circumference of the body.

In the illustrations of the preferred embodiments, the closure tool has been described as being used to close a surgical incision. The closure tools of the present invention may have application in closing non-surgical wounds as well. The stabilizer elements may be used to help retract the fascia away from internal organs for better visualization to determine whether any organs require repair. The closure tool can then be used to close the wound in the same manner described above.

We claim:

1. A device for assisting in closure of an incision in tissue layers of a patient, the device comprising:
    a cylindrical body defining a longitudinally extending side wall for introduction through the incision, the cylindrical body having a distal end portion, a proximal end portion, and a length between the distal end portion and the proximal end portion sized such that the distal end portion may be positioned adjacent an inner surface of an innermost tissue layer while the proximal end portion remains accessible outside the patient; and
    at least one wing element movably supported at the distal end portion, the at least one wing element being selectively movable between a retracted position to permit insertion of the cylindrical body through the incision, and a deployed position where the at least one wing element extends laterally away from the cylindrical body to permit contact with an interior surface of the innermost tissue layer,
    wherein the cylindrical body defines at least one guide channel extending from the proximal end portion to the distal end portion for directing a needle carrying a suture from an entry opening at the proximal end portion through an opening defined by the at least one wing element such that at least a portion of the suture passes through the opening of the at least one wing element, and
    wherein the cylindrical body further defines a slot extending through the side wall to allow lateral passage of the suture out of the at least one guide channel while preventing lateral passage of the needle.

2. The device of claim 1, wherein the at least one wing element is pivotally mounted to the distal end portion of the cylindrical body.

3. The device of claim 2, wherein the cylindrical body includes a lower edge and at least one leg extending therefrom, a distal end of the at least one leg defining a pivot mount for the at least one wing element.

4. The device of claim 3, wherein the cylindrical body includes a pair of legs extending from the lower edge, and wherein the pivot mount includes an axle extending between the pair of legs, the at least one wing element being rotatably mounted on the axle.

5. The device of claim 4, wherein the pivot mount includes a torsion spring engaged between the at least one wing element and the axle, the torsion spring being configured to bias the at least one wing element toward the deployed position.

6. The device of claim 1, further comprising an actuator supported at the distal end portion of the cylindrical body, the actuator being coupled to the at least one wing element to selectively actuate the at least one wing element between at least the retracted position and the deployed position.

7. The device of claim 6, wherein the actuator is connected to the at least one wing element via at least one actuator wire.

8. The device of claim 1, wherein the at least one wing element includes a pair of wings pivotably mounted toward the distal end portion of the cylindrical body.

9. The device of claim 8, wherein the pair of wings are substantially aligned with the cylindrical body in the retracted position and extend transversely outward from the cylindrical body in the deployed position.

10. The device of claim 1, wherein the at least one wing element is supported toward the distal end portion of the cylindrical body to be selectively movable to a removal position where the at least one wing element is substantially in alignment with the cylindrical body for removal of the cylindrical body through the incision.

11. The device of claim 1, wherein the entry opening is conical to facilitate introduction the needle carrying the suture into the at least one guide channel.

12. The device of claim 1, wherein the at least one wing element includes a rigid wing element configured to bear against the tissue from within an insufflated surgical site to provide pressure to compress the tissue during suture insertion.

13. The device of claim 1, wherein the at least one wing element includes a retention device at a free end thereof, the retention device including a resilient element that deforms upon passage of a needle tip of the needle therethrough and is configured to retain the needle tip.

14. The device of claim 13, wherein the resilient element includes a plurality of resilient flaps.

15. The device of claim 13, wherein the at least one wing element includes a rigid wing element configured to bear against the tissue from within an insufflated surgical site to provide pressure to compress the tissue during suture insertion, and
wherein the resilient element is provided within the rigid wing element.

16. A method for assisting in the closure of an incision in body tissue, the method comprising:
introducing a cylindrical body having a longitudinally extending side wall through the incision,
deploying a wing element between the body tissue and body structure adjacent the incision by actuating the wing element to a deployed position, the wing element including an opening,
pulling the cylindrical body away from the body structure to contact the body tissue while the wing element is in the deployed position, and
advancing a needle carrying a suture through at least one guide channel with a suture slot defined by the cylindrical body to direct the needle through the opening of the wing element, the suture slot extending through the longitudinally extending side wall to prevent lateral passage of the needle.

17. The method of claim 16, wherein the advancing the needle carrying the suture further comprises passing at least a portion of the suture through the opening of the wing element.

18. The method of claim 16 further comprising:
capturing the suture with the wing element, and
withdrawing the needle from the at least one guide channel.

19. The method of claim 18 further comprising:
retracting the wing element by actuating the wing element to a retracted position where the wing element is substantially in alignment with the cylindrical body, and
withdrawing the cylindrical body from the incision with the suture captured so that the suture forms a ligature through the body tissue at the incision.

20. A device for assisting in closure of an incision in tissue layers of a patient, the device comprising:
a cylindrical body defining a longitudinally extending side wall for introduction through the incision, the cylindrical body having a distal end portion, a proximal end portion, and a length between the distal end portion and the proximal end portion sized such that the distal end portion may be positioned adjacent an inner surface of an innermost tissue layer while the proximal end portion remains accessible outside the patient; and
at least one wing element movably supported at the distal end portion, the at least one wing element being selectively movable between a retracted position to permit insertion of the cylindrical body through the incision, and a deployed position where the at least one wing element extends laterally away from the cylindrical body to permit contact with an interior surface of the innermost tissue layer,
wherein the cylindrical body defines at least one guide channel extending from the proximal end portion to the distal end portion for directing a needle carrying a suture from an entry opening at the proximal end portion through an opening defined by the at least one wing element such that at least a portion of the suture passes through the opening of the at least one wing element,
wherein the at least one wing element includes a rigid wing element configured to bear against the tissue from within an insufflated surgical site to provide pressure to compress the tissue during suture insertion, and
wherein the at least one wing element includes a resilient element provided within the rigid wing element that deforms upon passage of a needle tip of the needle therethrough and the resilient element is configured to retain the needle tip.

* * * * *